(12) United States Patent
Hugel et al.

(10) Patent No.: US 8,132,268 B2
(45) Date of Patent: Mar. 6, 2012

(54) APPARATUS AND METHOD FOR THE DETECTION OF FORCES IN THE SUB-MICRONEWTON RANGE

(75) Inventors: Thorsten Hugel, München (DE); Michael Geisler, Hallbergmoos (DE)

(73) Assignee: Technische Universitaet Muenchen (DE)

( * ) Notice: Subject to any disclaimer, the term of this patent is extended or adjusted under 35 U.S.C. 154(b) by 219 days.

(21) Appl. No.: 12/497,364

(22) Filed: Jul. 2, 2009

(65) Prior Publication Data

US 2010/0011472 A1    Jan. 14, 2010

Related U.S. Application Data

(63) Continuation of application No. PCT/EP2008/050075, filed on Jan. 5, 2008.

(30) Foreign Application Priority Data

Jan. 5, 2007 (DE) .......................... 10 2007 001 797

(51) Int. Cl.
*G01Q 60/00* (2010.01)

(52) U.S. Cl. ........................................ 850/42

(58) Field of Classification Search .............. 850/59, 850/42, 61
See application file for complete search history.

(56) References Cited

U.S. PATENT DOCUMENTS

| | | | |
|---|---|---|---|
| 5,372,930 A * | 12/1994 | Colton et al. | 435/6 |
| 5,874,668 A * | 2/1999 | Xu et al. | 73/105 |
| 2004/0213910 A1* | 10/2004 | Cai et al. | 427/299 |

FOREIGN PATENT DOCUMENTS

| | | |
|---|---|---|
| DE | 19631326 A1 | 2/1998 |
| DE | 10208800 A1 | 9/2003 |
| EP | 0511662 A1 | 11/1992 |
| EP | 0727639 B1 | 8/1996 |
| EP | 0829722 A2 | 3/1998 |

OTHER PUBLICATIONS

Florin, E.L., Moy, V.T., Gaub, H.E.: "Adhesion forces between individual ligand-receptor pairs", Science, 264, p. 415-417 (1994).
Hanke, F., Livadaru, L., Kreuzer, H. J.: "Adsorption forces on a single polymer molecule in contact with a solid surface", Europhys. Lett., 69 (2), p. 242-248 (2005).
Ros, R., Schwesinger, F et al.: "Antigen binding forces of individually addressed single-chain Fv antibody molecules", PNAS, 95, p. 7402-7405 (1998).
Smith, D.A., Connell, S.D. et al.: "Chemical force microscopy: applications in surface characterisation of natural hydroxyapatite", Analytica Chimica Acta 479, p. 39-57 (2003).
Kolb, H.C., Finn, M.G., Sharpless, K.B., "Click Chemistry: Diverse Chemical Function from a Few Good Reactions", Angewandte Chemie Int. Ed. vol. 40, p. 2004-2021 (2001).

(Continued)

*Primary Examiner* — Jack Berman
*Assistant Examiner* — Eliza Osenbaugh-Stewart
(74) *Attorney, Agent, or Firm* — St. Onge Steward Johnston & Reens LLC (57) ABSTRACT

A force microscope for the detection of forces in the sub-micronewton range has a measurement head which is used to carry out a relative movement with respect to a sample holder and to which a carrier molecule is attached on which probe molecules are placed.

17 Claims, 4 Drawing Sheets

OTHER PUBLICATIONS

Chatellier, T., Senden, J. et al.: "Detachment of a single polyelectrolyte chain adsorbed on a charged surface", Europhys. Lett., 41, p. 303-308 (1998).

Hinterdorfer, P., Baumgartner, W et al.: "Detection and localization of individual antibody-antigen recognition events by atomic force microscopy", PNAS 93, p. 3477-3481 (1996).

Evans, E., Ritchie, K: "Dynamic Strength of Molecular Adhesion Bonds" Biophysical Journal, vol. 72, Apr. 1997, pp. 1541-1555.

Hugel, T., Grosholz et al.: "Elasticity of Single Polyelectrolyte Chains and their desorption from solid supports studied by AFM based Single Molecule Force Spectroscopy" Macromolecules, 34, p. 1039-1047 (2001).

Eckel R et al: "Identification of binding mechanism in single molecule-DNA complexes" Biophysical Journal Biophys. Soc USA, vol. 85, No. 3, Sep. 2003, pp. 1968-1973.

International Preliminary Report on Patentability; PCT/EP2008/050075; Jul. 6, 2009; 6 pages.

International Search Report and Written Opinion of the International Searching Authority; PCT/EP2008/050075; Apr. 3, 2008; 10 pages.

Ikai A: "Nanomechanics of Protein-Based Biostructures" Japanese Journal of Applied Physics, Japan Society of Applied Physics, Tokyo, JP, vol. 43, No. 11A, Nov. 2004, pp. 7365-7375.

Friedsam, C., Del Campo Becares, A. et al.: "Polymer Functionalized AFM tips for Long-Term Measurements in Single-Molecule Force Spectroscopy", ChemPhysChem. 5, p. 388-393 (2004).

Seitz, M., Friedsam, C., et al.: "Probing Solid Surfaces with Single Polymers" ChemPhysChem. 4, p. 986-990 (2003).

Meyer, E.E., Rosenberg, K.J., Israelach-Vili, J.: "Recent progress in understanding hydrophobic interactions", PNAS, 103, p. 15739-15746 (2006).

Kienberger F et al: "Recognition force spectroscopy studies of the NTA-His6 bond" Single Molecules Wiley-VCH Germany, vol. 1, No. 1, 2000, pp. 59-65.

Dammer, U., Hegner, M. et al.: "Specific antigen/antibody interactions measured by force microscopy", Biophys. J. 70, 2437-2441 (1996).

Hugel, T., Seitz, M: "The Study of Molecular Interactions by AFM Force Spectroscopy" Macromol. Rapid Commun. 22, p. 989-1016 (2001).

* cited by examiner

APPARATUS AND METHOD FOR THE DETECTION OF FORCES IN THE SUB-MICRONEWTON RANGE

CROSS-REFERENCE TO RELATED APPLICATIONS

The present application is a continuation of pending International patent application PCT/EP2008/050075 filed on Jan. 5, 2008, which designates the United States and claims priority of German Application No. 10 2007 001 797 filed on Jan. 5, 2007. The disclosure of this application is hereby incorporated by reference in its entirety, as part of the present disclosure.

FIELD OF THE INVENTION

The invention relates to an apparatus for the detection of forces in the sub-micronewton range with a measuring head with which a relative movement in relation to a sample holder can be carried out and to which at least one probe element is attached by which an adhesion force between a sample placed on the sample holder and the measuring head can be transferred.

Further the invention relates to a method for the detection of forces in the sub-micronewton range.

BACKGROUND OF THE INVENTION

Such an apparatus and such a method are known from EP 0 829 722 A2. Said known apparatus is an atomic force microscope (AFM). Said known atomic force microscope comprises a measuring tip acting as measuring head, which is coated, either directly or after application of a metal- or oxide layer, with one or more probe molecules. The measuring tip is brought into contact with the surface of the sample to be examined, and the force occurring during retracting is measured. Thereby qualitative differences in the interaction between probe molecules and surfaces can be measured.

A corresponding method for a chemically differentiating imaging by use of atomic force microscopy is known from EP 0 727 639 A1.

Such atomic force microscopes can be used for imaging the topography of surfaces as well as for measuring binding forces between antibodies and antigens, as well as for a chemically differentiating imaging. More detailed information is to be found in the publication of FLORIN, E. L., MOY, V. T., GAUB, H. E.: Adhesion forces between individual ligand-receptor pairs, Science, 264, 415 (1994), in the publication DAMMER, U., HEGNER, M. et al.: Specific antigen/antibody interactions measured by force microscopy, Biophys. J. 70, 2437 (1996) as well as in the publication SMITH, D. A., CONNELL, S. D. et al.: Chemical force microscopy: applications in surface characterisation of natural hydroxyapatite, Analytica Chimica Acta 479, 39 (2003).

Force plateaus in the force-distance curve were discovered and interpreted a few years ago. Initial experiments on this issue are described in the publication CHÂTELLIER, T., SENDEN, J. et al.: Detachment of a single polyelectrolyte chain adsorbed on a charged surface, Europhys. Lett., 41, 303 (1998), in the publication HUGEL, T., GROSHOLZ et al.: Elasticity of Single Polyelectrolyte Chains and their desorption from solid supports studies by AFM base Single Molecule Force Spectroscopy Macromolecules, 34, 1039 (2001), as well as in the publication HUGEL, T., SEITZ, M.: The Study of Molecular Interactions by AFM Force Spectroscopy Macromol. Rapid Commun. 22, 989 (2001). In the scope of these experiments, polymers were adsorbed to a surface and then pulled off with a functionalized measuring tip. Here, two problems occur. On the one hand, the tip is after a short time not usable anymore, because the reactive groups are saturated. On the other hand, several hundreds of force-distance curves have to be taken until an outright single molecule curve is measured, since not in every measurement a polymer is received by the measuring tip.

For solving these problems, several probe molecules were covalently bound to the measuring tip and then brought into contact with the surface. After a certain time the tip was pulled off from the surface and the balance force necessary for desorption was measured. This cycle could often be repeated several dozens of times. Experiments of this kind are described in the publication SEITZ, M., FRIEDSAM, C., et al.: Probing Surfaces with Single Polymers ChemPhysChem. 4, 986 (2003) and FRIEDSAM, C., DEL CAMPO BECARES, A. et al.: Polymer Functionalized AFM tips for Long-Term Measurements in Single-Molecule Force Spectroscopy, ChemPhysChem. 5, 388 (2004).

A further great problem with conventional methods consists in discerning the intramolecular forces to be measured from unspecific interactions, in particular from interactions between the measuring tip and the surface to be measured. This problem can be reduced by flexible linkers, but at the best in exceptional cases be resolved. Experiments of this kind are described in HINTERDORFER, P., BAUMGARTNER, W. et al.: Detection and localization of individual antibody-antigen recognition events by atomic force microscopy, PNAS 93, 3477 (1996) and in ROS, R., SCHWESINGER, F. et al.: Antigen binding forces of individually addressed single-chain Fv antibody molecules, PNAS, 95, 7402 (1998).

A theoretical explanation for the occurrence of the observed adhesion forces on the basis of statistical mechanics is for certain systems given in HANKE, F., LIVADARU, L., KREUZER, H. J.: Adsorption forces on a single polymer molecule in contact with a solid surface, Europhys. Lett., 69 (2), 242 (2005).

DE 102 08 800 A1 further describes a method for measuring adhesion properties with an atomic force microscope. It describes to use a frequency shift in the dynamic atomic force microscopy for measuring the adhesion. This is an indirect measuring, since the frequency-distance curves needs to be converted in a force-distance curve beforehand. Moreover, this method could only be demonstrated in ultra high vacuum.

In the field of medical technology, the inspection of the coating of implants is of particular importance, and on the chemical field so is the inspection of polymer coatings. In both application fields, until today atomic force microscopes have not been used.

Today there are existing several mechanical testing methods for examining the adhesion of different coatings though. But the application field is very restricted, in particular for polymer coatings, and involves some disadvantages. Almost all these testing methods are not non-destructive—for example a scratch test, a indentation test, a tensile test or a four-point-bending test—or can only be used restricted to organic coatings—for example an inflation method or a peeling method. In some cases, for example for a tensile test or a peeling test, the use of an adhesive is necessary, wherein it cannot be excluded that the solvent contained in the adhesive reacts with the organic coating. Due to the generation of stress zones, which is associated with the contact of the probe to the coating surface to be examined, the tests on the mechanical adhesion can hardly be carried out under the same conditions and with a satisfactory repetition rate. Due to plastic deformations of substrate and coating, which are generated by the measuring head of the majority of the experimental systems, the value experimentally found for the adhesion strength often differs from the actual value by several orders of magnitude. Quantitative statements concerning the adhesion can in all cases not be made without a high uncertainty.

SUMMARY OF THE INVENTION

Based on this prior art, the object of the invention is to provide an apparatus and a method for carrying out non-destructive measurements of the adhesion of coatings and compound materials under different environmental conditions.

This object is achieved by an apparatus and a method with the features of the independent claims. Preferred embodiments of the invention are given in the dependent claims.

In the apparatus, an elongate carrier, on which the probe element is placed, is attached to the measuring head, which can perform a relative movement in relation to the sample holder. In this context, the term 'elongate carrier' designates a carrier whose longitudinal dimension is exceeding the traverse dimensions in the stretched state. Moreover, when carrying out the measurement, a force plateau is detected which can be associated with the adhesion of the probe element to the sample. Thus, the adhesion of the probe element to the surface of the sample can be detected with high accuracy. Further, the apparatus and the method assure that the probe element is interacting with the sample, since the chemical composition of the carrier is known and effects which are caused by the adhesion of the carrier to the sample can be eliminated.

By arranging the probe element remote from both ends of the carrier, there is above the force plateau associated with the carrier generated another force plateau, whose level and length in relation to the force plateau associated with the carrier can be determined with high accuracy.

In a preferred embodiment, a multiplicity of probe elements are attached to the carrier. Thus, in a single measurement, there can be observed several adjoining force plateaus or at least force plateaus of sufficient length, and the measurement error can be reduced correspondingly.

Moreover, a monomeric probe molecule is preferably used for the probe element, since the apparatus and the method are particularly suitable for testing the adhesion of monomeric probe molecules which are small in comparison to polymers, for example medical agents or dye.

For the carrier, there is preferably used a carrier polymer, provided it has at least one binding possibility for the probe element. Synthesized spider silk, polypeptides, polylactides and polysaccharides or other biopolymers are considered particularly suitable.

The connection between the measuring head and the carrier is preferably accomplished with the aid of polyethylene glycol. Thereby the unwanted unspecific adhesion between measuring head and sample as well as the interaction of the probe element and the measuring head can be suppressed.

In the method for the detection of forces in the sub-micron-ewton range, the length of the force plateau can be surveyed for making sure that the elongate carrier and the probe elements are actually interacting with the sample.

Further, the difference between the level of the force plateau associated with the carrier and the force plateau associated with the probe element can be evaluated for determining the adhesion of the probe element to the sample. Particularly, if the adhesion of the carrier to the sample is known beforehand, the force plateau associated with the carrier can be used to calibrate the measurement and to reduce the measuring error.

BRIEF DESCRIPTION OF THE DRAWINGS

Further advantages and features of the present invention will become apparent from the following description in which embodiments of the invention are explained in detail in conjunction with the accompanying drawings; in the drawings:

FIG. 3 shows a diagram of the distribution of the level of the force plateaus for the measurement on which FIG. 2 is based;

DETAILED DESCRIPTION OF THE INVENTION

Figure 1:
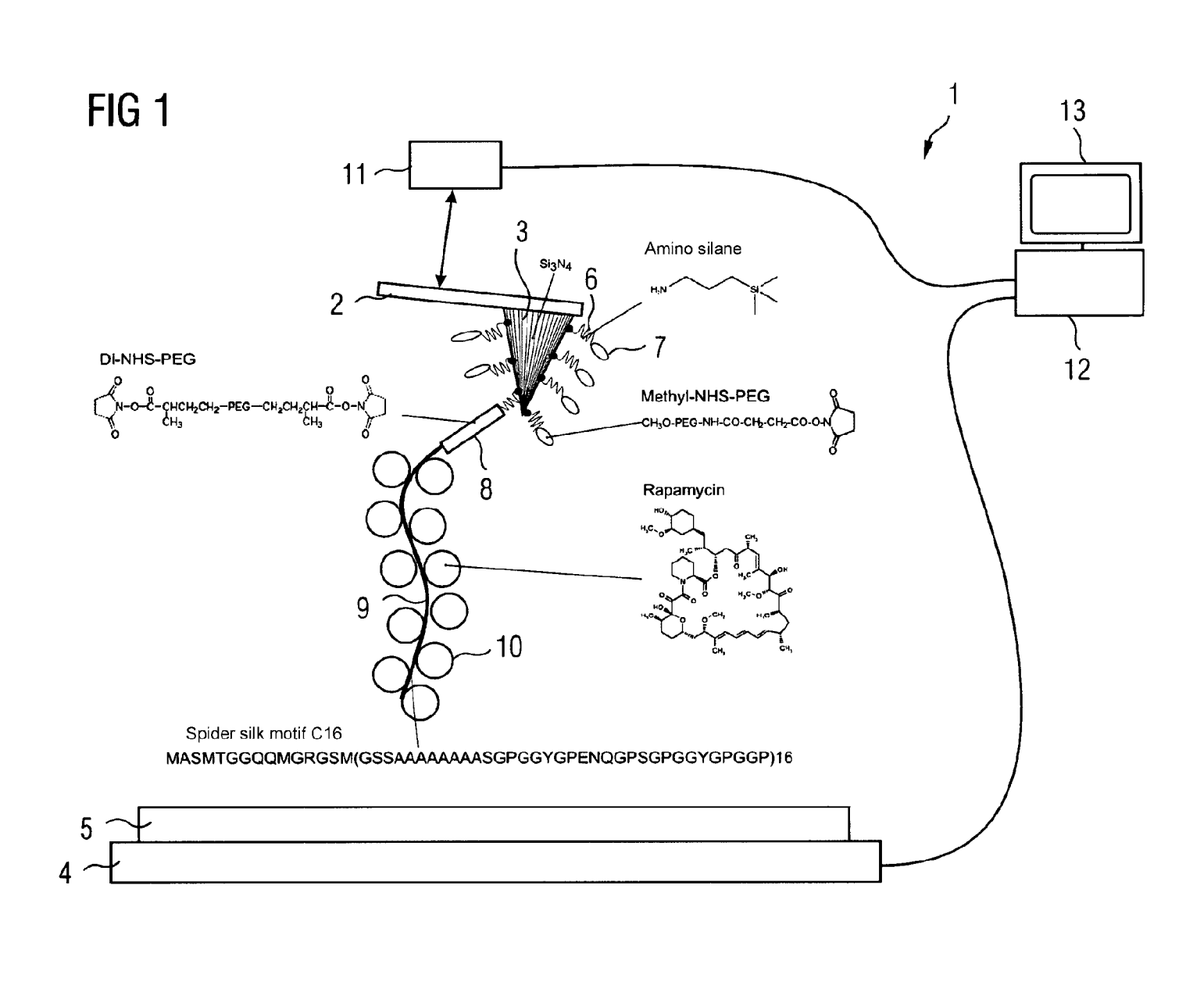
FIG. 1 shows an atomic force microscope whose measuring tip is provided with an elongate carrier molecule on which probe elements are laterally placed.

FIG. 1 shows an atomic force microscope 1 which comprises a measuring tip 3 attached to a cantilever 2. The atomic force microscope 1 further comprises a sample holder 4 on which is arranged a sample 5.

The measuring tip 3 is coated with activating molecules 6, which, for instance, may be amino silane as shown in FIG. 1. The free ends of the activating molecules are connected to passivating molecules 7 and connecting molecules 8. The connecting molecules 8 may, for instance, be methyl-NHS-PEG which has at its free end a methyl end group. On the contrary, the connecting molecules 8 are Di-NHS-PEG which have at both ends a succinimidyl end group. To the connecting molecule 8 can be attached a carrier molecule 9, for which, for instance, a synthesized spider silk can be used, in particular the spider silk motif C16. The length of the carrier molecule is typically less than 5 nm. Laterally attached to the carrier molecule 9 are probe molecules 10, for instance an agent molecule such as rapamycin. If the carrier molecule 9 or the probe molecules come into contact with the sample 5, an adhesion force is transferred between the measuring tip 3 and the sample 5, which causes a movement of the measuring tip 3. The movement of the measuring tip 3 can be detected with the aid of a distance sensor 11 whose measuring signal acts upon a control unit 12. The control unit 12, for example, can be a commercially available workstation computer with a monitor 13. The control unit 12 may also serve for moving the sample holder 4.

As mentioned above, for example, a synthesized spider silk can be used as carrier molecule 9. The polymer which is used in FIG. 1 as carrier molecule 9, i.e. spider silk motif C16, has 16 carboxyl groups to which an agent can be bound via its hydroxyl groups by means of a selective esterification.

Apart from the synthesized spider silk, other substances and substance groups can be considered to be used as carrier molecule 9, provided that they offer the possibility of a connection to the measuring tip 3 and the possibility of a connection to the probe molecules 10.

For example, polypeptides can be considered to be used as carrier molecules 9, provided that they allow a connection of the probe molecules. An example for this substance group is poly(glutamic acid), with which the same kind of chemical binding as for C16 is possible. Also polylactides are suitable to be used as the carrier molecule 9, since on the one hand they are often used as biocompatible polymer for the coating of medical products, and on the other hand they are commercially available in connection with agents. An example of this substance group is, for instance, the complex of poly(D,Llactid) and rapamycin which is used in the interventional cardiology as coating for stents.

The measuring tip 3, for example, can be prepared by coating the measuring tip 3 of the atomic force microscope 1, which is used as the adhesion probe, with a monolayer of polyethylene glycol (=PEG) of the same or of a different functionality, wherein the coating is carried out either directly, or after application of an oxide or metal layer, or after oxidation in plasma or in an acid bath with the aid of a silane, a thiol or a disulfide. The coupling of the carrier molecule 9 to PEG is effected via the covalent bond.

In detail, the measuring tip 3 can be prepared as follows: a measuring tip 3 made of silicon nitride is coated with an amino silane, after a wet chemical purification in a solution of concentrated sulfuric acid and potassium dichromate and after another fine purification and activation in oxygen plasma. This modified measuring tip is provided with another layer consisting of a mixture of methoxy-NHS-PEG (methyl end group) and a bifunctional Di-NHS-PEG (succinimidyl end groups). The molecular weights and the mixture ratios are adjusted such that a single carrier molecule 9 can be measured. By adding methoxy-PEG, the unwanted unspecific adhesion between measuring tip 3 and sample 5 as well as the interaction of the carrier molecule 9 and the measuring tip 3, is suppressed. Subsequently, the N-terminus of the synthesized spider silk motif C16 is bonded covalently to the still free binding sites of the Di-NHS-PEGs.

With the atomic force microscope 1 shown in FIG. 1, there can be carried out measuring methods with which an adhesion on molecular level can be detected. To this end, the atomic force microscope 1 is used with a single carrier molecule 9. This single carrier molecule 9 is specifically bound to the measuring tip 3, is brought into contact with the surface to be examined, and the force necessary to retract the carrier molecule 9 is measured. Under suitable conditions, in particular in aqueous environment, force plateaus in the force distance curve can be observed. The level of these force plateaus is extremely sensitive to the adhesion force between carrier molecule 9 and sample 5 and is independent of the force loading rate. In this context, the term 'force loading rate' designates the gradient of the force-time curve during retraction. Typically, the adhesion forces are in the range of 10 to several 100 piconewton. With the atomic force microscope 1, it is possible to measure minute differences in the adhesion of coatings.

It should be noted that the course of the force curve in the time axis of the retracting action is independent of the pulling speed. This is due to the fact that for the used pulling speeds of less than 1 mm/s quasi-equilibrium forces are measured.

The length of the force plateaus is substantially equal to the length of the carrier molecules 9. Further, the surface area of the force plateaus is substantially equal to the work that is performed during retracting the carrier molecule 9 and to the work and that corresponds to the work that has to be performed for transporting the carrier molecule 9 out of the surface potential well. Admittedly, the energy expended during retracting for stretching the carrier molecule 9 is not taken into account here.

The steady course of the force plateau becomes clearly comprehensible when one visualizes that on the stepwise retraction of the carrier molecule 9 the work performed is equal to the work that has to be performed for transferring a portion of the carrier molecule 9 from the free end of the carrier molecule 9 to the measuring tip 3.

Especially in medical technology, it is often necessary to release medical agents form a surface in a selective and time-controlled manner. With the atomic force microscope 1, it is possible to detect very fast the adhesion of medical agents on different sites and thereby find a surface having an optimal release behavior. In addition, with the apparatus here described, it is possible to examine the adhesion of substances used for surface coating, such as dyes.

The atomic force microscope 1 is especially suited for this purpose, since with the apparatus here described and the method here described, it is possible to examine the adhesion of monomeric molecules which are small in comparison to polymers. Most of the agents used for medical purposes fall under this category. However, also common dyes can be assigned to this category. If the probe molecules are directly bound to the measuring tip 3, a plateau in the force-distance curve can be observed. Therefore, a long molecule is used here as carrier molecule 9, to which one or many of the probe molecules 10 are bound, whose adhesion is to be observed and which are small in comparison to the carrier molecule. In particular for measurements using small molecules, it is advantageous if at least two of the probe molecules 10 are attached to the carrier molecule 9. When the probe molecules 10 have a sufficient size, occasionally a single probe molecule 10 can be sufficient, in particular if the single probe molecule 10 provides multiple bindungs to the sample 5.

In the following, various measurements will be explained in detail which were accomplished with a measuring tip 3 prepared according to FIG. 1.

Figure 2:
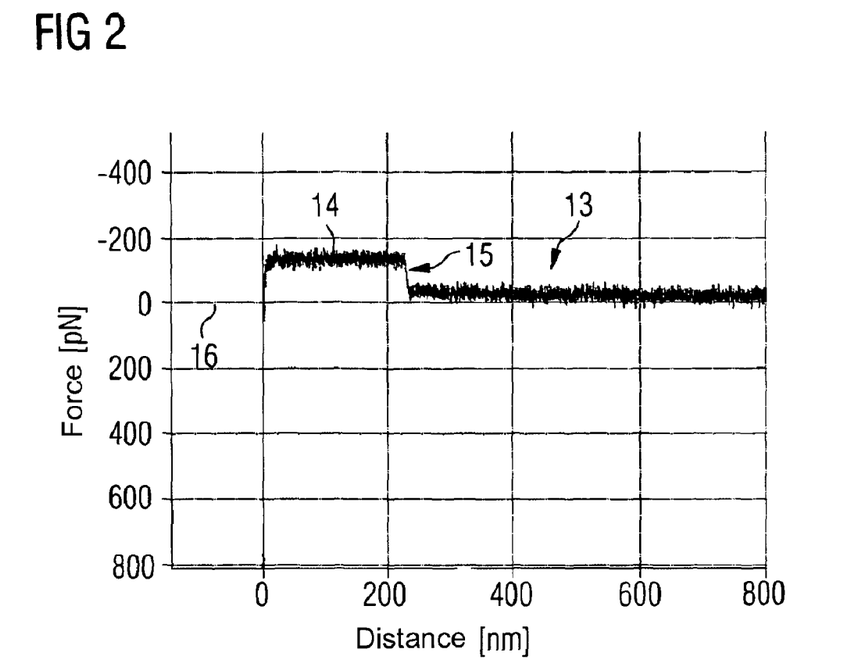
FIG. 2 shows a typical plateau in a force-distance curve for the desorption of a carrier molecule from the surface of a sample.
Figure 3:
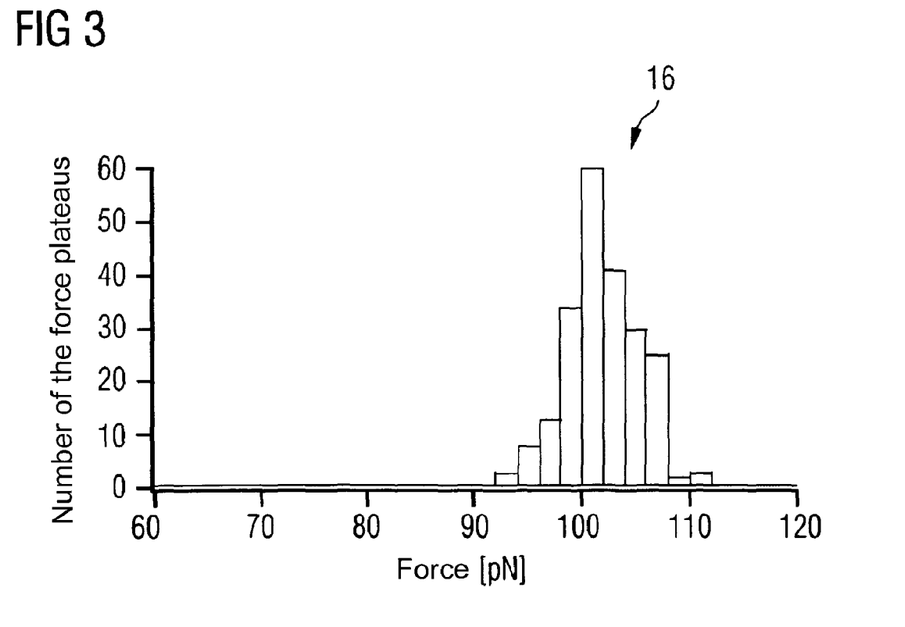

In the FIGS. 2 and 3, results of measurements are shown which were carried out with a single polymer carrier molecule 9. In particular the adhesion strength of the spider silk molecule, in particular of the spider silk motif C16 with a specified length of 230 nm, was examined in aqueous solution on a hydrogen terminated diamond surface. In a typical time scale (here 1 μm/sec), there were taken force-distance curves on different locations of the sample, and the measured force plateaus were evaluated with regard to length and desorption force. In FIG. 2, for example, there is shown a force-distance curve 13 with a force plateau 14. Herein, a drop 15 onto a zero level 16 indicates the separation of the carrier molecule 9 from the surface of the sample 5.

It should be noted that the force-distance curve 13 is essentially determined by the force plateau 14. This circumstance is due to an optimization of the utilized measuring tip 3 by which an interaction between the measuring tip 3 and the carrier molecule 9 is excluded.

FIG. 3 shows a distribution of plateau levels for 220 plateaus in the experiment of FIG. 1.

Figure 4:
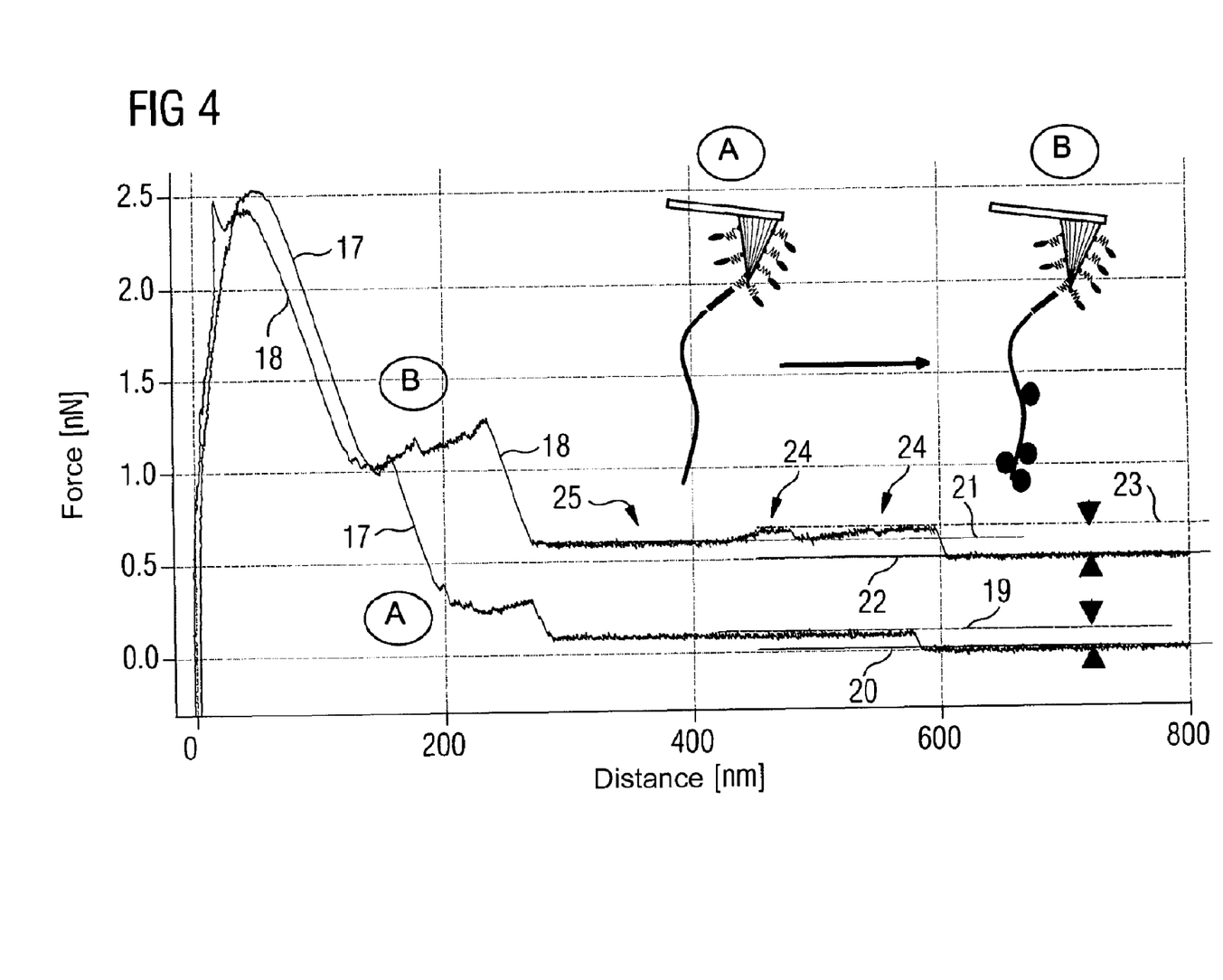
FIG. 4 shows a diagram of force-distance curves which were taken with and without probe molecules.
Figure 5:
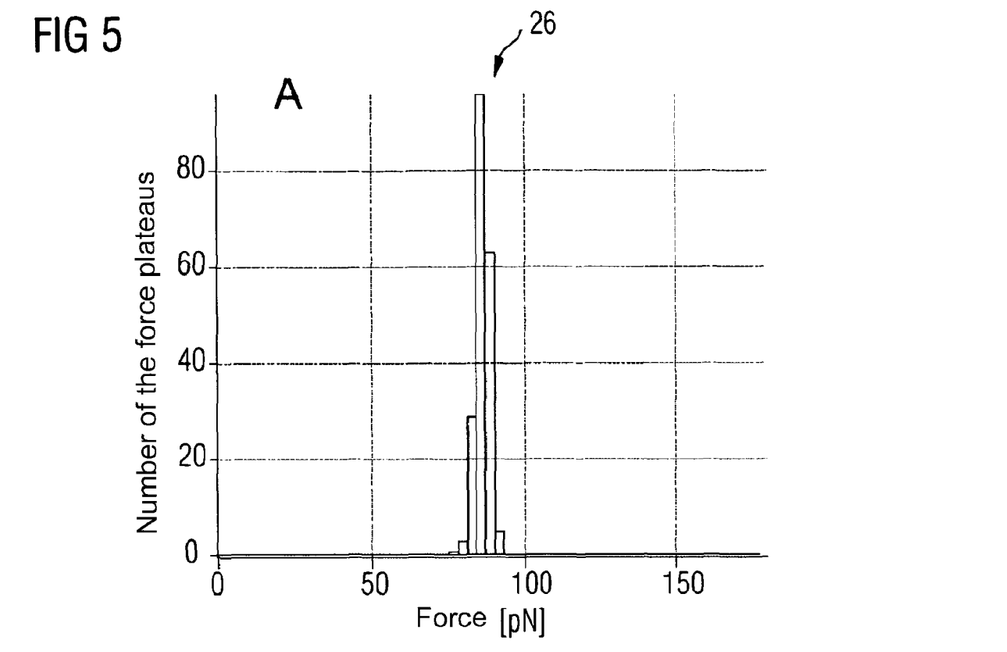
FIG. 5 shows a diagram of the distribution of the level of force plateaus for a measurement without probe molecules.
Figure 6:
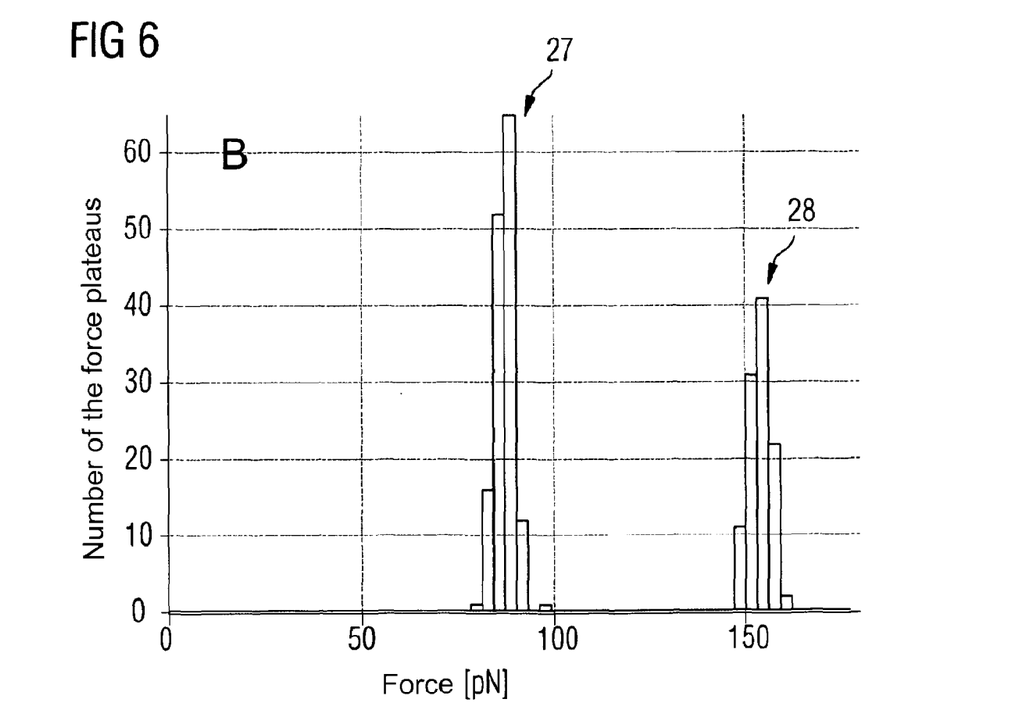
FIG. 6 shows a diagram of the distribution of the level of force plateaus for the measurement with probe molecules.

Further, in the FIGS. 4 to 6, the results of an experiment are shown in which firstly the adhesion of a carrier molecule 9, namely polyallylamine, to a hydrogen terminated diamond surface (A) is measured and then the adhesion to the same surface of the same carrier molecule 9 by means of dye molecules (B) is determined. The dye molecules are molecules of the dye Promofluor 555 of the company PromoKine.

The measurements were carried out in a PBS-buffer at about 37° C. to demonstrate the suitability for medically relevant molecules.

In FIG. 4, for comparison purposes are shown two desorption curves 17 and 18 of polyallylamin of H-diamond at 36.5° C. in PBS without (A) and with (B) Promofluor 555 molecules.

For the desorption curve 17, the plateau force results from the difference of a plateau line 19 to a zero line 20.

In the desorption curve 18, the plateau force pertaining for the carrier molecule 9 can firstly be determined from the difference of plateau line 21 and zero line 22. The binding of smaller probe molecules 10 having a stronger adhesion results in a shift of the plateau line to the plateau line 23. The increased adhesion force $F_{Des}$ can thus be measured by the increase of the plateau force.

The shift of the plateau line 23 is caused by the occurrence of additional force plateaus 24 which are situated above the force plateau 25, which is to be associated with the desorption of the carrier molecule 9 from the surface of the sample 5. The additional force plateaus 24 are caused by the desorption of the probe molecules 10 from the surface of the sample 5.

FIGS. 5 and 6 show, by way of comparison, the force distribution of polyallyl amine without (A) and with (B) Promofluor 555, respectively. While the force distribution shown in FIG. 5 for the case (A) shows a single peak 26, the force distribution of FIG. 6 for the case (B) shows two peaks 27 and 28.

The average value of the peak 26 shown in FIG. 5 is at about 86 piconewton. The adhesion force of the pure carrier polymer is therefore at about 86 piconewton. This corresponds to a desorption energy of about 7 $k_B T$ (=3×10$^{-20}$ Joule) per amino acid.

FIG. 6 shows the force distribution for the case in which the reactive dyes (Promofluor 555, Mw=793 Dalton, PromoK-ine) are bound to exactly this carrier polymer, and again the plateau forces were determined. According to FIG. 4, additional higher force plateaus 24 occur, and thus, in addition to the first peak 27 pertaining to the desorption of the carrier molecule 9, a second peak 28 of the distribution of the plateau levels shown in FIG. 6 with an adhesion force of about 153 piconewton occurs. This corresponds to a desorption energy of more than 12 $k_B T$ (5×10$^{-20}$ Joule) per amino acid.

It should be noted that the plateau level of the carrier polymer as such which corresponds to the plateau line 21 in FIG. 4 is still clearly identifiable, since it is not completely occupied with fluorophores. The adhesion force, and thus the desorption energy has considerably changed, though.

This experiment shows, in which way the adhesion force of a single carrier polymer is changed by binding small probe molecules 10, in particular dyes, to exactly this carrier polymer. In this case, the adhesion force on the hydrophobic surface is increased as expected, since the dye is more hydrophobic than the carrier polymer. This confirms that, in fact, the adhesion of the probe molecules 10 was measured in an equilibrium measurement, and not only the adhesion of the carrier polymer.

It should further be noted that a polymer with known length is preferably used as carrier molecule 9, whereby a reliable intrinsic control is provided so that the genuine adhesion between probe molecule 10 and surface, which has to be examined, is measured.

It should further be noted that the force plateau 25 which is attributable to the desorption of the carrier molecule 9 can be used for calibrating the desorption curve 18, since the desorption energy necessary for the desorption of the carrier molecule 9 is usually known from previous measurements.

Thereby, the error in the determination of the desorption energy necessary for the desorption of the probe molecules 10 can be significantly reduced.

By virtue of the smaller error, the apparatus can be used for measuring the very short ranged (<1 nm) regime of the hydrophobic force. Until today, there has not been a technique for measuring this, and there are indications, for example in MEYER, E. E., ROSENBERG, K. J., ISRAELACH-VILI, J.: Recent progress in understanding hydrophobic interactions, PNAS, 103, 15739 (2006), that the force in this regime is considerably larger than in the previously measured, medium and long ranged regimes of the hydrophobic force.

The fact that these forces can actually be measured in the atomic force microscope 1 is shown by first measurements on various surfaces having different ion and buffer strengths. Here, on hydrophobic surfaces were observed force differences which cannot be explained by electrostatic or other long ranged forces.

The apparatus and the method can be modified in various ways.

Instead of an atomic force microscope, it is possible to use other apparatuses for the measurement of forces in the sub-micronewton range. Such apparatuses are for example nanoidenters, optical tweezers, magnetic tweezers, or other apparatuses for detecting surface forces.

Instead of a single polymer, it is possible to use several polymers as carrier molecules, as long as there is a force plateau in the force-distance curve, as it is to be expected, for instance, in triple-stranded poly(glycine-valine-glycine-valine-proline).

Instead of esterification, there can be used other covalent bonds to bind the probe molecule to the carrier molecule. In particular, here the so-called Click-Chemistry is to be mentioned. Detailed information concerning Click-Chemistry can be found for example in KOLB, H. C., FINN, M. G., SHARPLESS, K. B., Click Chemistry: Diverse Chemical Function from a Few Good Reactions, Angewandte Chemie Int. Ed. Vol. 40, 2004 (2001).

Further, instead of a plateau in the force-distance curve, there can be used other characteristic features on the force-distance curve, for example the chair-boat-transition of polysaccharides, or series of force plateaus on different levels.

Further it is possible, to carry out a plurality of measurements in parallel. For instead of a single measuring tip, it is possible to use several measurement tips simultaneously.

It should be emphasized that the measuring tip is preferably to be modified such that the carrier molecule does not interact with the measuring tip.

Further it is noted that, for a first rough characterization, it can also be useful to use the three following discrete forms of the force-distance curve during retracting of the measuring tip: for example, it is possible to evaluate the course of the initial elevation in the desorption curve 18, or to excerpt additional information from the ramp-like course of the desorption curve 18 before the drop at a distance of 250 nm.

By using the probe molecule as carrier molecule for smaller non-polymeric molecules, due to the detection of adhesion forces, the methods described herein can be used in the field of screenings of agents, and in particular due to the possibility to couple a multiplicity of probe molecules 10 to the carrier molecule 9, also for a mass screening of agents. The measuring tip 3 loaded with an agent will here be used on a suitable sample with immobilized receptors. The faster detection of interaction forces with the aid of the present method, which is due to a measurement in equilibrium, has to be mentioned here as great advantage in comparison to existing methods. Also the inverse case is possible in which a probe loaded with receptor molecules is desorbed by a sample loaded with an agent.

Another application in the field of biotechnology and pharmaceutics consists in the use of organic acids in polymeric form, such as DNA or RNA as probe molecules. By analyzing the force plateaus, the nucleic acid sequence along the polymer chain can be determined. DNA or RNA strands can also be sequenced by firstly immobilizing the DNA or RNA molecules to be tested on a sample holder, by coupling the complementary bases to a carrier polymer, and by measuring their adhesion according to the method described herein.

The apparatuses and the methods described herein have several additional advantages:

At first, it has to be emphasized that the atomic force microscope works in various environments, for example physiological conditions, room temperature, or atmospheric pressure.

As described above, the measured binding force depends of the force loading rate. This dependency has not been taken into consideration in conventional methods, in particular in the methods known from EP 0 727 639 A1 and EP 0 829 722 A2. Consequently, it was necessary to take hundreds of pull-off curves with different force loading rates and to correlate them for obtaining a meaningful quantitative value for the adhesion. As illustrated by the narrow force distribution shown in FIG. 3 within an experiment, in the apparatus and method described herein, a single force curve is basically sufficient for measuring the exact adhesion force.

As has been mentioned at the beginning, it is a great problem with conventional methods to discern the intramolecular forces to be measured from unspecific interactions, in particular from interactions between the measuring tip and the surface to be measured. This problem can be reduced by flexible linkers, but will only be solved in exceptional cases. On the contrary, the specified length of the polymer used as carrier molecule which has to correspond to the length of the force plateau is a reliable indicator that the measured force really is the force that is acting between the probe molecule and the surface.

Another problem of conventional methods is that the surface and coating of the measuring tip is never exactly the same on the molecular level. Rather, the coating is inhomogeneous on the molecular level. Thus, with two identically prepared measuring tips, different pull-off forces would be measured. With the method here described, every measuring tip gives the same result in the measuring of a force plateau, because a single polymer is 100% pure. Furthermore the stability of the probe could be shown for many hundred force curves. Thus, the method here described allows to measure a variety of samples by using one and the same molecule and to thereby generate an optimal comparability and reproducibility of the results.

With the method of the prior art, the adhesion of coatings can only be measured with large restrictions. Rather, the known measuring methods are methods which provide rough estimates. Insofar an industrial use of the known methods appears to be of little sense. On the contrary, with the method here described not only the adhesion of polymers, but also of molecules such as various commercially available medical agents or dyes can be determined.

Finally, it should be noted that features and characteristics which have been described in conjunction with one particular embodiment can be combined with another embodiment, except if this is excluded for compatibility reasons.

Lastly, it should be noted that throughout the description and claims of this specification, the singular encompasses the plural unless the context otherwise requires. In particular, where the indefinite article is used, the specification is to be understood as contemplating plurality as well as singularity, unless the context requires otherwise.

What is claimed is:

1. An apparatus for the detection of forces in the sub-micronewton range comprising a measuring head, with which a relative movement in relation to a sample holder can be performed and on which at least one probe element is attached, by which an adhesion force between a sample placed on the sample holder and the measuring head can be transferred, wherein an elongate carrier, on which the probe element is placed, is attached to the measuring head, and wherein a force plateau associated with the adhesion of the probe element to the sample can be detected by an evaluation unit that is capable of detecting the relative movement between said measuring head and said sample holder and wherein the probe element is placed on the carrier remote from both ends of the carrier and wherein at least two probe elements are placed on the elongate carrier.

2. The apparatus according to claim 1, wherein a multiplicity of probe elements is placed on the elongate carrier.

3. The apparatus according to claim 1, wherein the probe element is a monomeric molecule.

4. The apparatus according to claim 3, wherein the probe element is a medical agent or a dye.

5. The apparatus according to claim 1, wherein the carrier is a carrier polymer with binding possibilities for the probe element.

6. The apparatus according to claim 5, wherein the carrier polymer has a predetermined length.

7. The apparatus according to claim 5, wherein the carrier polymer is made on the basis of a biopolymer.

8. The apparatus according to claim 1, wherein the measuring head is coated with polyethylene glycol.

9. The apparatus according to claim 1, wherein the force plateau associated with the adhesion of the probe element is an additional force plateau situated above a force plateau, which is associated with the desorption of the elongated carrier.

10. An apparatus for the detection of forces in the sub-micronewton range comprising a measuring head, with which a relative movement in relation to a sample holder can be performed and on which at least one probe element is attached, by which an adhesion force between a sample placed on the sample holder and the measuring head can be transferred, wherein an elongate carrier, on which the probe element is placed, is attached to the measuring head, and wherein a force plateau associated with the probe element can be detected by an evaluation unit that is capable of detecting the relative movement between said measuring head and said sample holder and wherein the probe element is placed on the carrier remote from both ends of the carrier, wherein at least two probe elements are placed on the elongate carrier, and wherein the carrier polymer is made on the basis of a synthesized spider silk, a polypeptide, a polylactide, or a polysaccharide.

11. A method for the detection of forces in the sub-micronewton range, wherein the distance between a measuring head provided with a probe element and a sample is varied and a relation to an adhesion force acting between the measuring head and the sample is determined using a probe element which is placed on an elongate carrier attached to the measuring head, wherein a force plateau is detected, which can be associated with the adhesion of the probe element to the sample, and wherein a probe element is used which is attached to the elongate carrier remote from both ends of the carrier.

12. The method according to claim 11, wherein a monomeric probe molecule is used as a probe element.

13. The method according to claim 11, wherein as a carrier a carrier polymer with a binding possibility for the probe element is used.

14. The method according to claim 11, wherein a carrier having a predetermined length is used.

15. The method according to claim 11, wherein the length of a force plateau associated with the carrier is surveyed.

16. The method according to claim 11, wherein the difference of the level of a force plateau of the probe element to the level of the force plateau of the carrier is evaluated.

17. The method according to claim 11, wherein the force plateau associated with the adhesion of the probe element is an additional force plateau situated above a force plateau, which is associated with the desorption of the elongated carrier.

* * * * *